United States Patent [19]

Ewing et al.

[11] Patent Number: 5,320,730

[45] Date of Patent: Jun. 14, 1994

[54] CAPILLARY ELECTROPHORESIS APPARATUS WITH IMPROVED ELECTROOSMOTIC FLOW CONTROL

[75] Inventors: Andrew G. Ewing; Mark A. Hayes; Indu Kheterpal, all of State College, Pa.; Steven S. Herrick, Anaheim Hills, Calif.

[73] Assignees: The Penn State Research Foundation, University Park, Pa.; Beckman Instruments, Inc., Fullerton, Calif.

[21] Appl. No.: 7,677

[22] Filed: Jan. 22, 1993

[51] Int. Cl.$^5$ .............................................. C25B 9/00
[52] U.S. Cl. ............................ 204/299 R; 204/180.1; 204/182.1
[58] Field of Search .............. 204/180.1, 182.1, 299 R

[56] References Cited

U.S. PATENT DOCUMENTS

| | | | |
|---|---|---|---|
| 5,092,972 | 3/1992 | Ghowsi | 204/182.1 |
| 5,151,164 | 9/1992 | Blanchard et al. | 204/182.1 |
| 5,180,475 | 1/1993 | Young et al. | 204/180.1 |

OTHER PUBLICATIONS

"High Performance Electrophoresis, Elimination Of Electroendosmosis and Solute Adsorption", Hjerten, Journal of Chromatography, 347 (1985), pp. 191-198.
"Analytical Chem.", Hayes et al., vol. 64, (1992) pp. 512-516.
"Capillary Electrophoresis", Ewing et al., Analytical Chemistry, 1989, vol. 61, 292A.
"Capillary Electrophoresis", Kuhr, Analytical Chemistry, 1990, vol. 62, 403R-414 R.
"Direct Control of the Electroosmosis in Capillary Zone Electrophoresis by Using an External Electric Field", Lee et al., Analytical Chemistry, 1990, vol. 62, pp. 1550-1552.

Primary Examiner—John Niebling
Assistant Examiner—C. Delacroix-Muirheid
Attorney, Agent, or Firm—Thomas J. Monahan

[57] ABSTRACT

An electrophoretic separation apparatus includes a capillary tube having a length, a cross section, an inlet and an outlet. A first reservoir containing a solvent and, upon injection, a solute is in fluid-flow communication with the inlet and a second reservoir containing at least a solvent is also in fluid flow communication with the outlet, the capillary thereby being filled at least with the solvent. A first power supply means applies a separation potential between the first and second reservoirs and along the length of the capillary to thereby establish an electrophoretic flow of the solute therethrough. An electrically isolated plate is juxtaposed to an external surface of the capillary tube and is connected to a second power supply. An electrostatic field is thereby applied across the cross section of the capillary tube to control the electroosmotic flow therein. The electrical isolation of the plate prevents current flow between the power supply and the plate. The plate achieves effective electroosmotic flow control even though it extends only over a small portion of the length of the capillary tube.

4 Claims, 5 Drawing Sheets

CAPILLARY ELECTROPHORESIS APPARATUS WITH IMPROVED ELECTROOSMOTIC FLOW CONTROL

FIELD OF THE INVENTION

This invention relates to capillary electrophoresis instruments and, more particularly, to an improved system for controlling electroosmotic flow velocities in the capillary of a capillary electrophoresis instrument.

BACKGROUND OF THE INVENTION

This patent application is related to U.S. patent application Ser. No. 08/077,214, filed on even date and having a common title herewith.

Zone electrophoresis in capillaries is widely used to accomplish liquid-phase separations of various solutes. Capillary electrophoresis has been used for separation of small and large molecules, various amino acids, alkylamines and various proteins. In brief, a zone capillary electrophoresis device includes a buffer filled capillary tube that is placed between two buffer reservoirs. A potential field is applied across the length of the capillary tube and ionic solutes in one buffer reservoir then differentially migrate through the capillary into the other reservoir. Small diameter silica based tubes are employed as the capillaries in capillary zone electrophoresis (CZE) instruments.

A distinguishing property of flow through a capillary is electroosmotic flow. Immediately adjacent to the solid-liquid interface at the interior of the silica-based capillary wall, a stagnant double layer of solute/solvent is found. Under normal aqueous conditions, the silica capillary wall surface has an excess of charge resulting from an ionization of surface functional groups. Thus, SiOH groups are ionized leaving $SiO^-$ at the wall surface and $H^+$ ions in the solution and in the stagnant double layer adjacent to the capillary wall. This action creates a potential across the layers which is termed the zeta potential. The zeta potential is dependent upon the viscosity of the fluid, the dielectric constant of the solution and the coefficient of electroosmotic flow of the solution. The cationic counter ions ($H^+$) in the diffuse solvent/solute layer migrate towards the cathode and because these ions are solvated, they drag solvent with them. The extent of the potential drop across the double layer governs the rate of flow. It is known that control of electroosmotic flow is effective in improving electrophoretic resolution and efficiency and is a controlling factor in obtaining reproducible results in CZE apparatus.

The prior art evidences a number of ways to alter electroosmotic flow. Hjerten indicates that inner surfaces of a capillary can be derivatized by coating them with a mono-molecular layer of non-cross-linked polyacrylamide. This coating encourages the osmotic effect and discourages adsorption of solutes onto the inside of the capillary. See "High Performance Electrophoresis, Elimination of Electroendosmosis and Solute Adsorption", Hjerten, Journal of Chromatography, 347 (1985), pp. 191-198. Others have taught that electroosmotic flow may be altered by altering the buffer pH, the concentration of the buffer, the addition of surface-active species such as surfactants, glycerol, etc. or various organic modifiers to the buffer solution.

For additional details regarding capillary electrophoresis instrumentation and methods of control of electrophoretic separation, the following papers provide a useful oversight of the field: "Capillary Electrophoresis", Ewing et al., Analytical Chemistry, 1989, Volume 61, 292A and "Capillary Electrophoresis", Kuhr, Analytical Chemistry, 1990, Volume 62, 403R-414R.

Independent control of electroosmotic flow (i.e., not related to changes in the buffer or inner capillary structures) have been accomplished by application of external electric fields. As indicated above, it is known that separation resolution can be enhanced and protein adsorption prevented by dynamically controlling the polarity and magnitude of the zeta potential at the boundary between the aqueous fluid and the capillary wall. Lee et al. in "Direct Control of the Electroosmosis in Capillary Zone Electrophoresis by Using an External Electric Field", Analytical Chemistry, 1990, Volume 62, pp. 1550-1552, employ an additional electric field from outside the capillary to enable external control of the zeta potential. Lee et al. mounted a capillary tube inside another tube, filled the annular space therebetween with a potassium phosphate buffer and applied high voltage across the annular space to achieve an electric field along the entire length of the capillary. A pump was used to provide fluid flow of the potassium phosphate buffer to enhance transfer of the heat created by current flow through the buffer. It was determined that by varying the electric field, changes in both the direction and flow rate of electroosmosis in the inner capillary could be achieved. In U.S. Pat. No. 5,151,164, to Blanchard and Lee, the concepts disclosed in the aforementioned Lee et al. article are expanded to include a non-aqueous conductive member surrounding capillary along its entire length.

Hayes et al., "Analytical Chem.", Vol. 64, (1992) pp. 512-516, have achieved a similar control of electroosmotic flow by the application of a radial voltage field about the length of the capillary, but avoided the necessity for an annular fluid flow region as taught by Lee et al. Hayes et al. coated the exterior surface of a capillary with a flexible conductive polymer sheath and then applied a voltage thereacross to achieve a radial field effect within the capillary. Both Hayes et al. and Lee et al. teach the control of electroosmotic flow via an applied radial voltage field and depend upon an application of a radial voltage to all or nearly all of the length of the electrophoresis capillary. Furthermore, all employ a current flow in the material surrounding the capillary to achieve the radial electric field. Such current flows create additional Joule heating within the capillary which adds to the Joule heating that occurs as a result of current flow through the buffer (caused by the voltage applied across the capillary to achieve electrophoretic flow). As is also apparent from the prior art, all flow control fields taught in the prior art were of the electrodynamic variety wherein the fields were created by a current flow in a conductive media adjacent the capillary.

Accordingly, it is an object of this invention to provide an improved system for controlling electroosmotic flow in CZE apparatus.

It is another object of this invention to provide an electroosmosis control structure for a CZE apparatus which is readily manufacturable.

It is yet another object of this invention to provide an electroosmotic flow control system for CZE apparatus which avoids creation of unnecessary Joule heating of the capillary.

SUMMARY OF THE INVENTION

An electrophoretic separation apparatus includes a capillary tube having a length, a cross section, an inlet and an outlet. A first reservoir containing a solvent and, during injection, a solute is in fluid-flow communication with the inlet and a second reservoir containing at least a solvent is also in fluid flow communication with the outlet, the capillary thereby being filled at least with the solvent. A first power supply applies a separation potential between the first and second reservoirs and along the length of the capillary to thereby establish an electrophoretic flow of the solute therethrough. An electrically isolated plate is juxtaposed to an external surface of the capillary tube and is connected to a second power supply. An electrostatic field is thereby applied across the cross section of the capillary tube to control the electroosmotic flow therein. The electrical isolation of the plate prevents current flow between the power supply and the plate. The plate achieves effective electroosmotic flow control even though it extends only over a small portion of the length of the capillary tube.

DETAILED DESCRIPTION OF THE INVENTION

Figure 1:
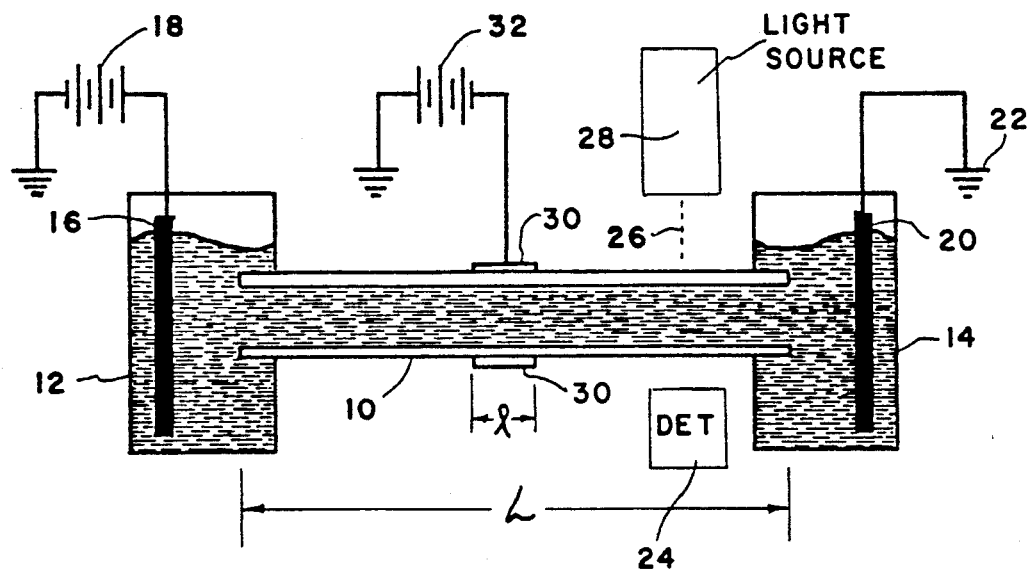
FIG. 1 is a schematic drawing of a CZE separation apparatus with a capillary coated with conducting silver paint that is connected to an externally applied potential.

Referring now to FIG. a schematic drawing of a CZE apparatus is shown that includes a capillary 10 and first and second reservoirs 12 and 14. Reservoirs 12 and 14 are each filled with a solvent. Reservoir 12 also temporarily contains an injected solute that is to be separated by electrophoretic action. Within reservoir 12 is an electrode 16 that is connected to a power supply 18. Reservoir 14 has a similar electrode 20 that is connected to a source of reference potential 22.

Separation within capillary 10 is detected by changes in light absorption across capillary tube 10. Those changes are detected by detector 24 that determines variations in the luminance of a light beam 26 emanating from a light source 28. The structure described to this point is conventional and is well known to those skilled in the art of CZE.

In contrast to the prior art, this invention controls electroosmotic flow through capillary 10 by application of a large voltage to a relatively small length, non-grounded conductor along the outside of capillary 10. In brief, the electrically isolated (i.e., non-grounded) nature of the conductor enables creation of an electrostatic field across the capillary while preventing current flow in the conductor that could create Joule heating. Such electroosmotic flow control is achieved in one embodiment of the invention by applying a small annulus 30 of a metallic paint (or other conductive coating) about the external circumference of capillary 10. A power supply 32 is connected to annulus 30 and causes the creation of an electrostatic potential across the cross section of capillary 10.

As will become hereinafter apparent, it has been determined that the length 1 of conductive annulus 30 can vary between wide limits (e.g., from approximately 5% to more than 60% of the length of capillary 10) without significantly affecting the ability to control electroosmotic flow through capillary 10. As a result, it has been found that the length 1 of annulus 30 can be made very short with respect to the overall length L of capillary 10, while still enabling control of the electroosmotic flow therethrough.

Figure 2:
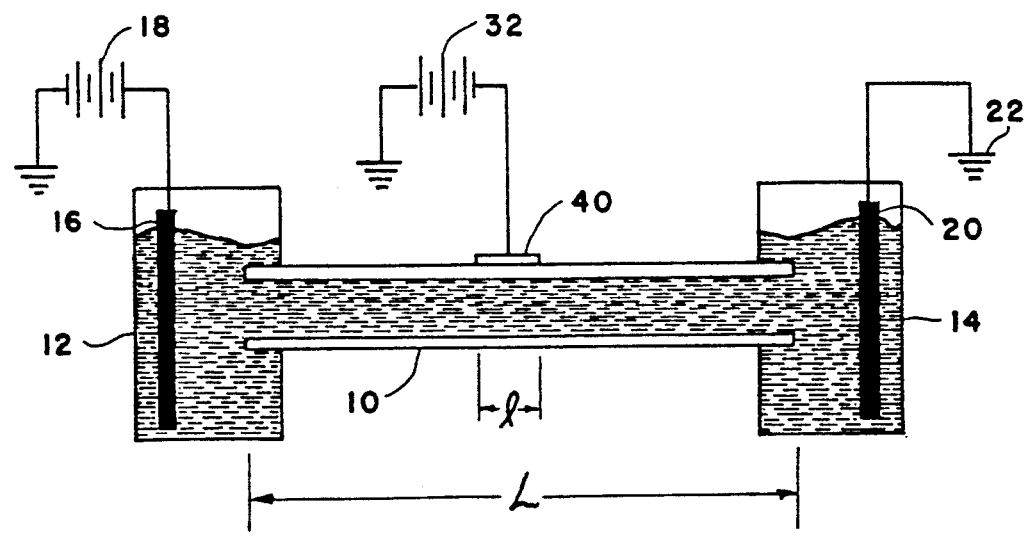
FIG. 2 is a schematic drawing of a CZE separation apparatus with a metal plate covering a small segment of the center of the capillary.
Figure 3:
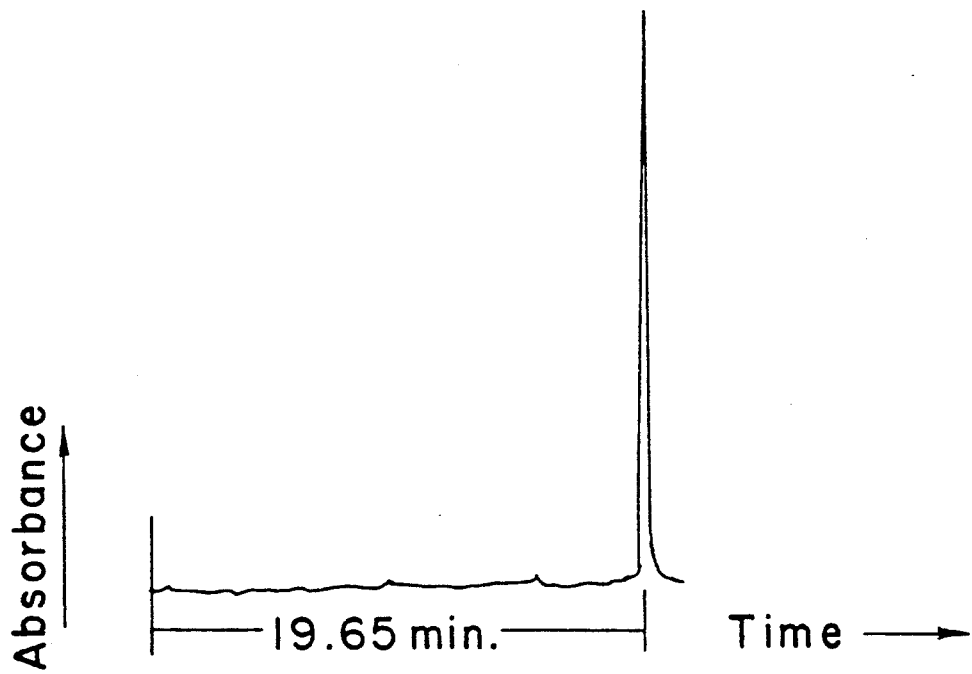
FIG. 3 plots absorption versus time to determine a migration peak for a neutral solute (phenol) obtained without control of electroosmotic flow.
Figure 4:
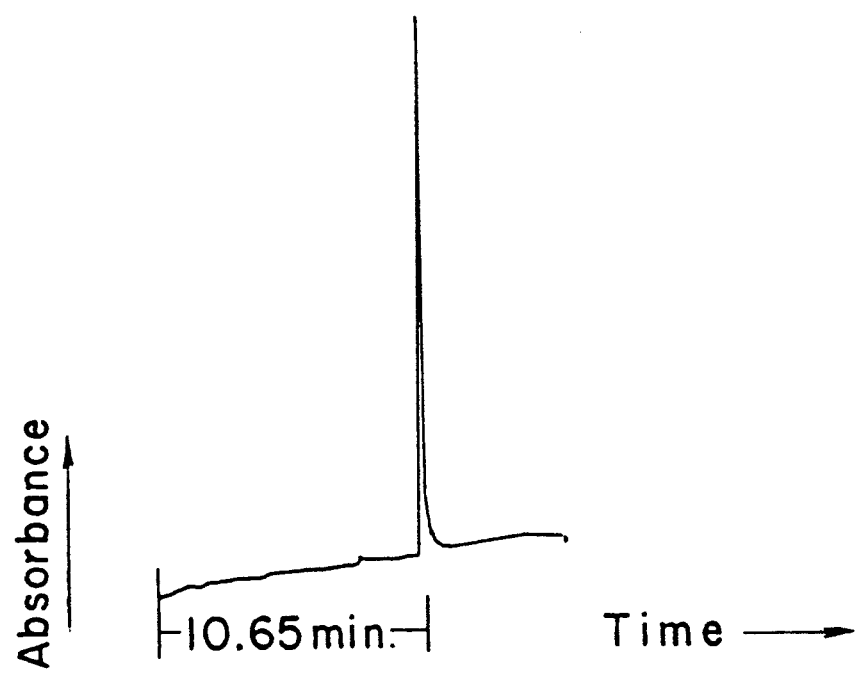
FIG. 4 is a plot of absorption versus time to obtain a migration peak for neutral solute (phenol) obtained with control of electroosmotic flow using an external potential field applied to a capillary coated with an encircling region of conductive paint such as shown in FIG. 1.
Figure 5:
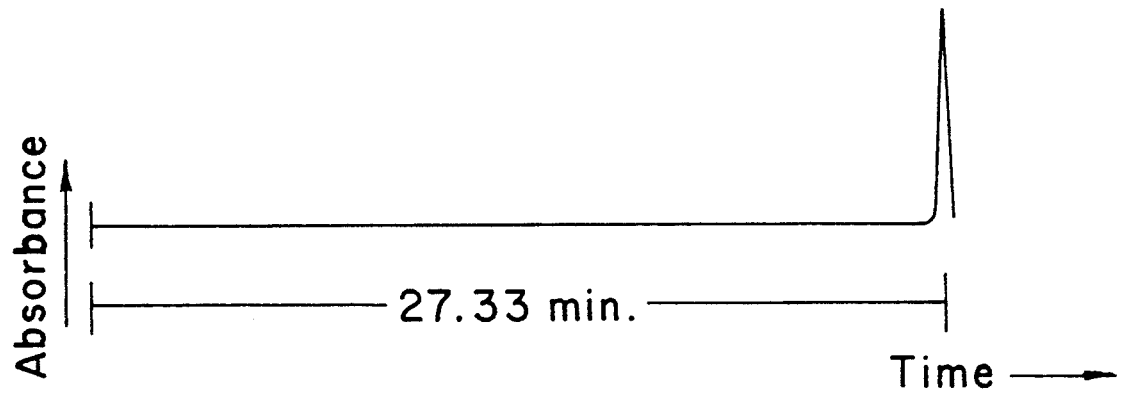
FIG. 5 is a plot of adsorbents versus time to determine a migration peak for a neutral solute (phenol) obtained without control of electroosmotic flow.
Figure 6:
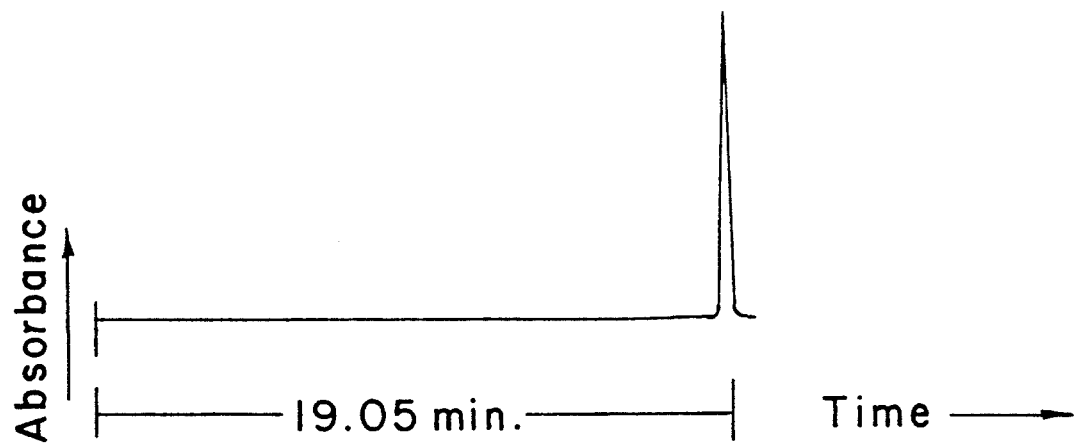
FIG. 6 is a plot of absorption versus time to determine a migration peak for a neutral solute (phenol) obtained with control of electroosmotic flow using an external potential field applied to a conductive plate adjacent the capillary, such as is shown in FIG. 2.

Referring to FIG. 2, a substantially identical CZE apparatus is shown except that annulus 3 has been replaced by a flat plate 40 that contacts only a small portion of the circumference of capillary 10. The length of plate 40 can be similarly proportioned to the overall length of capillary 10 as is the proportion of annulus 30 to capillary 10 in FIG. 1, and still effectively control electroosmotic flow through capillary 10.

In both FIGS. 1 and 2, power supply 32 is indicated as applying a control potential to annulus 30 and plate 40, respectively. The control potential has the effect of controlling (e.g., speeding up) flow of solute through capillary 10, thereby enabling a substantial increase in the speed of separation. By altering the control potential, the electrophoretic action can be speeded up, stopped or reversed For instance, when the control potential is at a high negative value, electrophoretic action is substantially accelerated. As will become apparent from the detailed experimental description below, the electroosmotic control apparatus shown in FIG. 1 (power supply 32 and conductive annulus 30) reduces separation time by almost 50% when compared to a system without electroosmotic flow control. The structure shown in FIG. 2 enables a decrease in separation time of approximately 30% when compared to a system without electroosmotic flow control.

EXPERIMENTAL

The separation capillary is a 20 um i.d., 144 um o.d. fused silica microcolumn with a length of 52.5 cm for silverpaint coating experiments and 50 um i.d., 370 um o.d. with a length of 57 cm for the experiments with a stainless steel plate (Polymicro Technologies, Phoenix, Arizona). Reversible high voltage power supplies (Spellman, Plainview, NY) were used to apply the voltages across the capillary and to the conductors outside the capillary.

Voltages applied to the inlet of the capillary ranged from 0 to 30 kV with the outlet of the separation capillary at ground potential. Voltages applied to the conductor outside the model of the capillary ranged from 0 to ±20 kV.

Capillary 10 is liquid-filled with electrolyte and terminates just after passing through a Linear 200 absorbance detector (Linear Instruments, Reno, NE). All aspects of this experiment are common to capillary electrophoresis experiments with the exception that this apparatus allows the application of a high potential to a conductor along a relatively short outer segment of capillary 10.

Apparatus.

The system used two plexiglas interlock boxes to house the high potential field portions of the capillary. The high potential lead for the separation potential and the injection end of the polyimide-coated fused silica capillary were enclosed in the first box. The second box contained the portion of the capillary coated with conducting silver paint or a conducting plate.

An ultraviolet detector (Linear 200, Reno, NE) was installed on-line. Approximately 6 cm from one end of the capillary a 1-cm section of the polyimide coating was removed by heat as a UV detection window. Data was collected at a wavelength of 200 nm.

Chemicals.

Solutions were made from $NaH_2PO_4$ (Sigma Chemical, St. Louis, MO) and adjusted to the desired pH with $H_3PC_4$ (Baker Chemical, Phillipsburg, NJ) or NaOH. Histidyl phenylalanine (Sigma Chemical Co.) was used as a probe molecule.

RESULTS

The effect of a radial voltage in capillary electrophoresis across the capillary wall on eleotroosmotic flow created by a conductive sheath covering only a small portion of the capillary has been examined. These experiments have been related to the double layer and surface conductivity inside the capillary.

Electroosmotic flow can be altered by chemical modification of the capillary wall and by adjustment of buffer pH. Electroosmotic flow can also be controlled electronically by the application of a radial voltage field. The prior art teaches the application of a radial voltage field over a majority of the length of the capillary. The theory developed by the prior art has assumed that the radial voltage effects the flow only in those portions of the capillary covered by the sheath providing the radial voltage field. In the experiments presented here, a relatively small portion of the outside center of the capillary is covered with a conductive silver paint (or a metal plate) and attached to a 0-30 kV power supply. Using this configuration, it has been found that electroosmotic flow may be controlled to a similar extent as with the prior art systems. The results apparently defy previous theories on the electronic and molecular mechanism of electroosmotic flow control. Theory and experiments are presented, however, to suggest that surface conductance along the inside surface of the capillary leads to a double layer potential that is distributed over sections of the capillary outside the area of direct radial voltage coverage. Thus, an applied radial voltage over a small portion of the capillary (at substantially any point along its length) has been found sufficient to effectively control electroosmotic flow.

The radial voltage field created by a conductive sheath effects the zeta ($\zeta$) potential on the inner surface of the capillary. This $\zeta$ potential is related to electroosmotic flow ($v_{eo}$) by $v_{eo}\zeta D_o E_{app}/\eta_o$, where $D_o$ is the permittivity of the solution, $\eta_o$ is the viscosity of the solution and $E_{app}$ is the separation potential field. Various lengths of the center portion of the capillary have been coated, followed by experimental evaluation of the electroosmotic flow.

Under the experimental conditions, according to current theory, a zone of high flow rate at the inner wall along this coated region would be generated, effectively forming a pump in the middle of the capillary. Application of the prior art model leads to a prediction of varied flow rates along the capillary when electroosmotic flow is increased (or decreased) in the region of the applied radial voltage. The slower (or faster) moving buffer in unsheathed portions of the capillary is expected to lessen the effectiveness of the radial voltage control. In such a model, the bulk flow across the capillary is the weighted average of the sheathed and unsheathed flow zones. This results( in the following relationship (Chien, Helmer, *Anal. Chem.* 63 (1991) 1354-1361):

$$v_b = x v_s + (1-x) v_{us}, \qquad (1)$$

where $v_b$ the bulk electroosmotic flow, x is the portion of the capillary covered by the sheath, $v_s$ is the flow with 100% sheath coverage and $v_{us}$ is the flow without any sheath.

The change in electroosmotic flow rate has been evaluated by examining the elution time of a neutral solute from the capillary as a function of the potential applied to the conductor in contact with the capillary. FIGS. 3-6 show eluting peaks compared for applied voltages at a capillary coated with conducting silver paint (FIG. 4) and a capillary in contact with a metal plate (FIG. 6), respectively. Those results show that an externally applied potential to only a relatively small portion of the capillary can effectively control electroosmotic flow (as compared to non controlled flows (i.e., see FIGS. 3 and 5). The effect of contacting different fractions of the capillary on the ability to control electroosmotic flow have also been examined.

Figure 7:
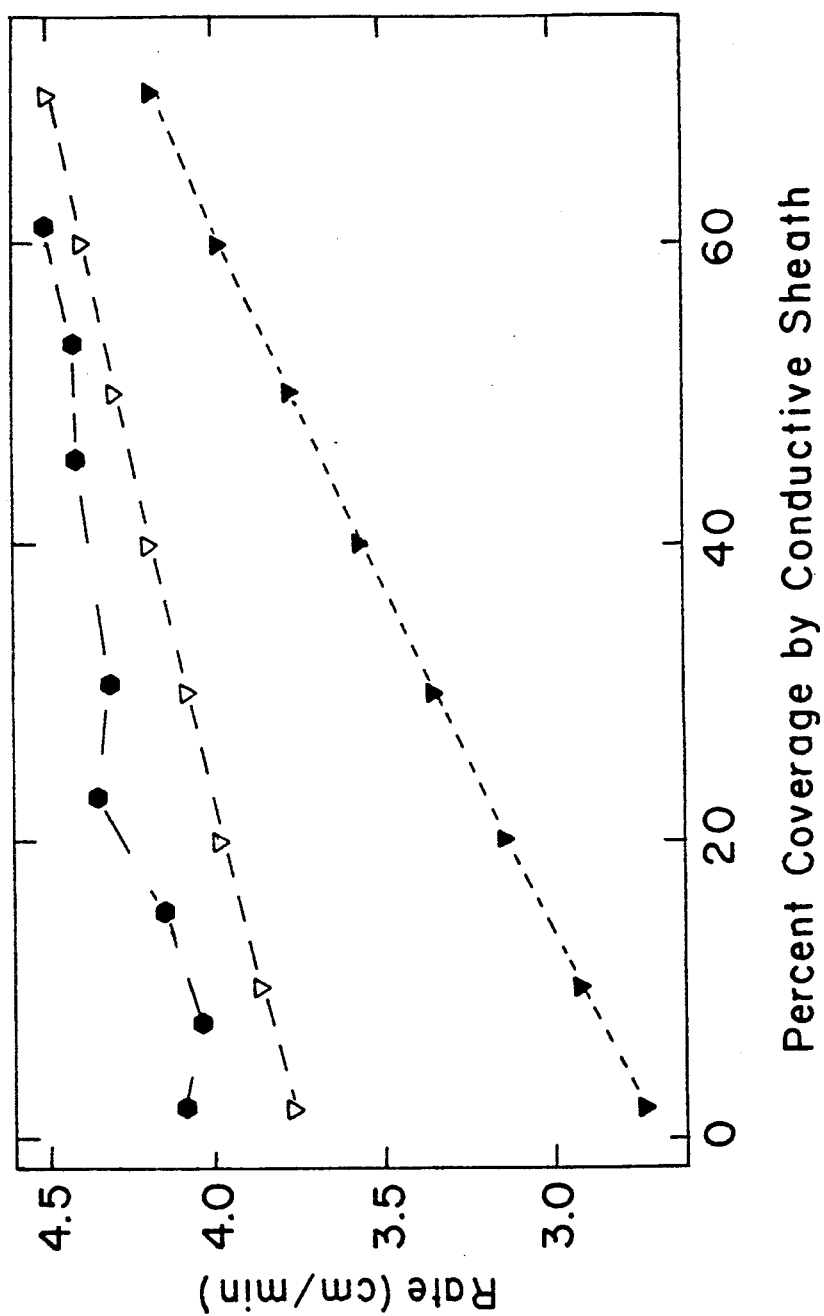
FIG. 7 is plot showing variation in migration rates for a neutral solute (histidyl-phenylalanine) versus percent coverage by the conductive sheath and comparing experimental data to two theoretical predictions.

Data for these experiments are plotted and compared to theory in FIG. 7. The experimental data ( ) is compared to predictions derived from the literature and summarized in equation 1 ( ). In this experiment, the effect of electroosmotic flow generated in the unsheathed portions of the capillary on the overall flow is significantly smaller than that predicted by the original theory, both in magnitude and slope of the resulting plot.

An explanation for the deviation from accepted theory is that the charge induced by the radial voltage in only a small percent of the capillary is dispersed over the entire double layer on the inner surface of the capillary. Thus, the $\zeta$ potential varies less than predicted between sheathed and unsheathed regions.

Figure 8:
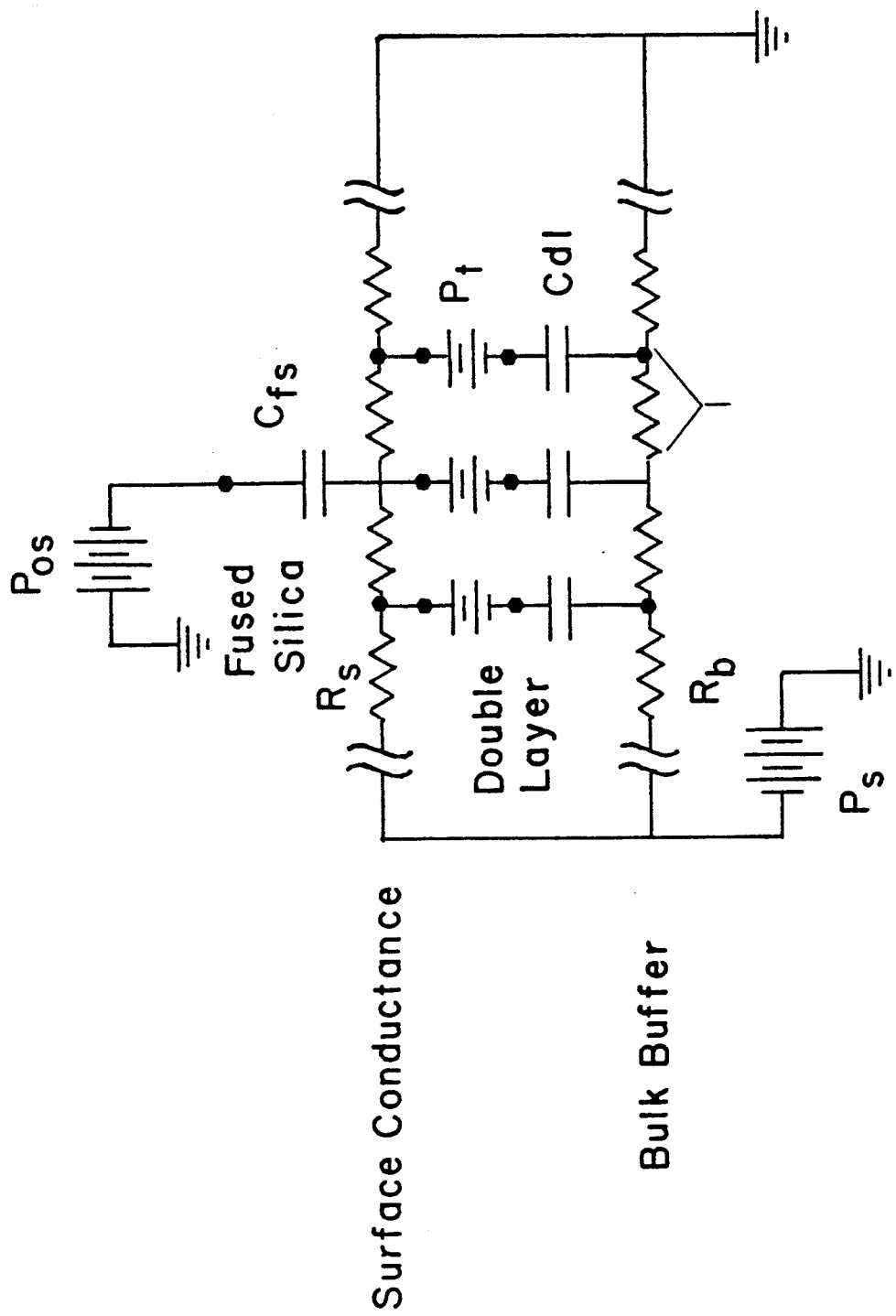
FIG. 8 is an equivalent circuit for the electroosmotic flow control apparatus shown in FIGS. 1 and 2.

Modification of existing theory to include a surface resistance (or conductance) can account for this new experimental evidence. This new model (FIG. 8) accounts for the separation potential, bulk buffer resistance, outer sheath potential, and the fused silica capacitance with the addition of a resistor along the inner surface, Rs, and the realization that the potential generated by the ionized silanol groups occurs at all points along the capillary. This modification to the theory may be quantitated. A surface conductance ($R_s$) along the double layer interface has been documented (Sheludko, *Colloid Chemistry*, Elsevier, Amsterdam, 1966; Overbeek, In "Colloid Science", Vol. 1, Kruyt, Ed., Elsevier, Amsterdam, 1952, pp. 197–237) and has been estimated at the glass/water interface to be $10^{12}$–$10^{13}$ $\Omega/m$. In addition, the potential caused by the ionization of the surface silanol groups, may be calculated and is a complex function of buffer pH and other physical properties of the buffer/inner surface interface (e.g. Hayes, Ewing Anal. Chem. 64 (1992) 512–516). The model indicates that the additional surface charge from the radial voltage is effectively spread along the inner surface of the capillary through $R_s$ and directly effects the $\zeta$ potential over the entire capillary length. This effect can be quantitated by assuming the $\zeta$ potential forms a linear gradient through $R_s$ from $\zeta_s$ (100% sheathed, $v_s$) in the center to $\zeta_{us}$ (unsheathed, $v_{us}$) at the ends, across the unsheathed portions of the capillary. In the sheathed sections, the potential is equal to $\zeta_s$. Since the flow is directly proportional to $\zeta$, the average flow, $v_{ave}$, in the unsheathed sections is $(v_s+v_{us})/2$. this average velocity may be substituted into equation 1 to give a new relationship for the fraction of capillary covered by the conducting sheath, x, versus bulk electroosmotic flow, $v_b$;

$$v_b = xv_s + (1-x)v_{ave} \qquad (2)$$

The plot of equation 2 in FIG. 7 ($\nabla$) more closely reflects the experimental values than the plot of equation 1 ( ). In fact, the slope of the experimental data is even smaller than that predicted by theory, even accounting for conductance along the inner surface of the capillary. The data make a strong case for a spreading of the $\zeta$ potential along the inner wall of the capillary.

The design for electronic control of electroosmotic flow in a capillary electrophoresis system requires application of only a small section of silver paint (or a conductive plate) to the outside surface of the capillary and only one power supply. It has been found with silica capillaries that have uncoated internal surfaces, that the buffer should preferably have a pH in the acidic range. If the buffer is basic, control of electroosmotic flow is difficult. However, by applying a non-absorptive coating on the capillary's interior, a higher pH buffer is usable. Such a coating may be dextran, polyimides, polyethylene glycols, etc.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Electrophoretic separation apparatus comprising:
   capillary tube means having a length, a cross section, an inlet and an outlet;
   a first reservoir for containing a solvent and, upon injection, a solute, in fluid flow communication with said inlet;
   a second reservoir for containing at least a solvent, in fluid flow communication with said outlet, said capillary thereby filled with at least said solvent when solvent is present in a reservoir;
   first power supply means for applying a separation potential between said reservoirs and along the length of said capillary to establish an electrophoretic flow of said solute therethrough;
   a flat conducting plate in contact with an external surface of said capillary tube means, said contact occurring along a line parallel to the length of said capillary tube means; and
   second power supply means for applying a voltage to said plate that creates an electrostatic field in said capillary tube means said electrostatic field controlling electroosmotic flow through said capillary tube means.

2. The electrophoretic separation apparatus as recited in claim 1 wherein said flat conducting plate is electrically isolated from any reference potential and is solely connected to said second power supply means.

3. The electrophoretic separation apparatus as recited in claim 2, wherein said capillary tube means has a length L and said flat conducting plate has a length 1, said length 1 being between approximately 5% to 60% of length L.

4. The electrophoretic separation apparatus as recited in claim 1, wherein said capillary tube means has an interior surface that is coated with a non-absorptive coating.

* * * * *